United States Patent [19]

Hache et al.

[11] Patent Number: 4,619,505
[45] Date of Patent: Oct. 28, 1986

[54] REFRACTOMETRY PROCESS AND DEVICE FOR MEASURING THE DEGREE OF AMETROPIA, AND ESPECIALLY THE DEGREE OF ASTIGMATISM, OF THE EYE

[75] Inventors: Jean C. Hache, Lille; Mireille Servant, Villeneuve d'Ascq, both of France

[73] Assignee: Essilor International (Compagnie Generale d'Optique), Creteil, France

[21] Appl. No.: 610,632

[22] Filed: May 16, 1984

Related U.S. Application Data

[63] Continuation-in-part of Ser. No. 442,588, Nov. 8, 1982, abandoned.

[30] Foreign Application Priority Data

May 19, 1983 [FR] France .................................. 83 08281

[51] Int. Cl.⁴ .............................................. A61B 3/10
[52] U.S. Cl. ...................................... 351/211; 351/205

[58] Field of Search ............... 351/205, 210, 211, 212, 351/213, 216, 217

[56] References Cited

U.S. PATENT DOCUMENTS 3,791,719 2/1974 Kratzer et al. ...................... 351/217

Primary Examiner—Rodney B. Bovernick
Assistant Examiner—P. M. Dzierzynski
Attorney, Agent, or Firm—Burgess, Ryan & Wayne

[57] ABSTRACT

The invention concerns a process and device for measuring the degree of ametropia of an eye.

The rays of a luminous source passes through a focussing lens and a test lens in order to create an image on the retina. The rays issuing from the source or from the image pass through a black optical slit and are reflected by at least one reflecting surface defined in a revolving screen driven in rotation by a motor.

Application to refractometric instruments for measuring the degree of ametropia of the eye.

5 Claims, 4 Drawing Figures

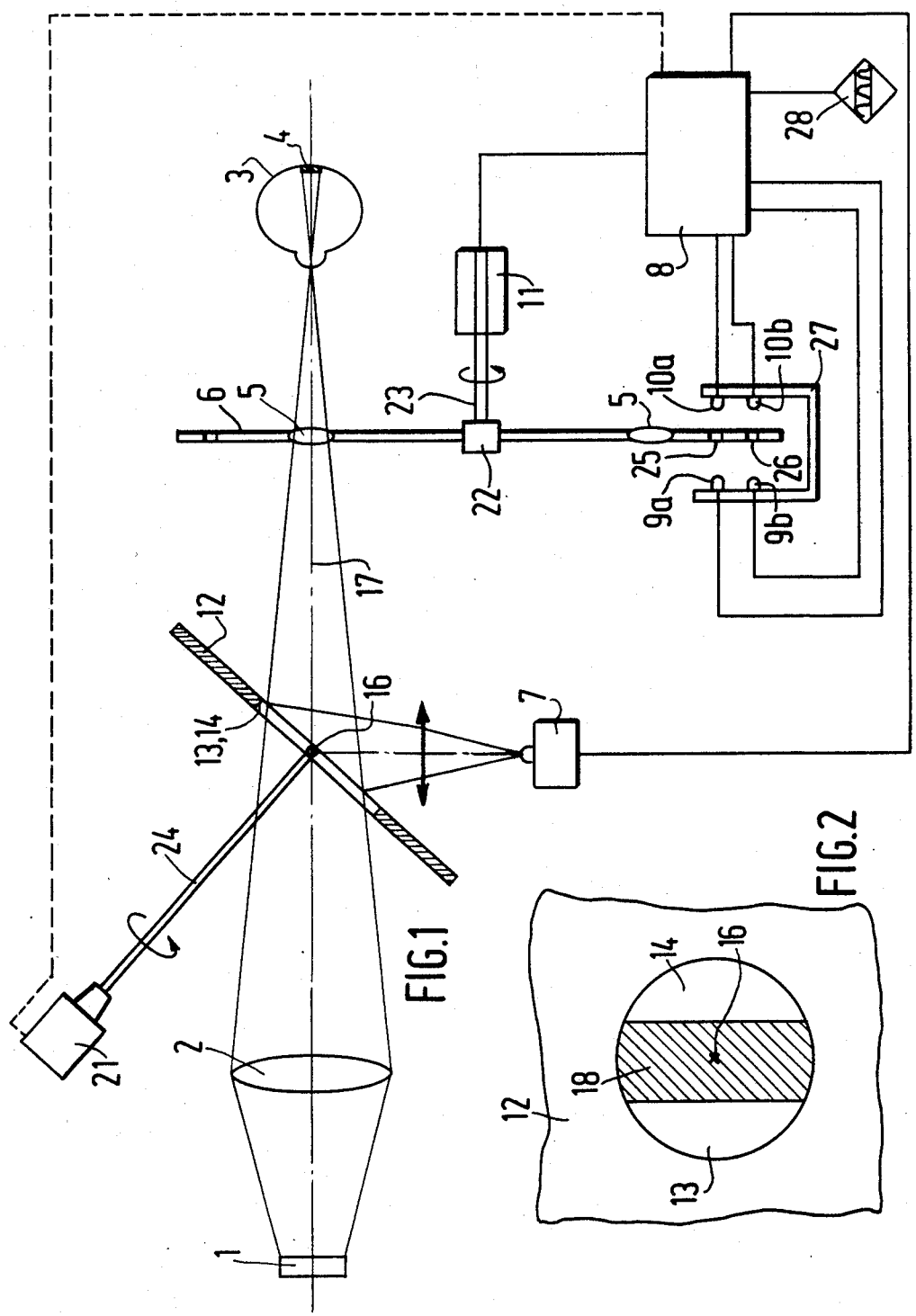

REFRACTOMETRY PROCESS AND DEVICE FOR MEASURING THE DEGREE OF AMETROPIA, AND ESPECIALLY THE DEGREE OF ASTIGMATISM, OF THE EYE

REFERENCE TO RELATED APPLICATION

This application is a continuation-in-part of U.S. patent application Ser. No. 06/442,588, filed on Nov. 8, 1982, to the same applicant herein, now abandoned.

BACKGROUND OF THE INVENTION

The present invention concerns a refractometry process and a device for measuring the degree of ametropia and especially the degree of astigmatism of an eye.

SUMMARY OF THE INVENTION

The invention concerns more particularly a process of refractometric measurement of the degree of ametropia and astigmatism of an eye, that consists in causing luminous rays, issuing from a light source, to pass through a focussing lens presenting predetermined optical characteristics, towards the retina of the eye to be examined, in order to create an image of the said source, to collect, in a fixed plane, by means of a luminous intensity detector, the rays emitted by the said image, the respective optical axes of the source and of the detector being shifted angularly with respect to each other, to interpose on the path of the rays focussed by the focussing lens and the rays emitted by the said image; successively, a plurality of test lenses of different respective optical powers, and to identify that of the test lenses which, when it is interposed, causes to coincide at least substantially the punctum remotum of the eye with the said fixed plane and thus provokes a minimum luminosity signal of the said detector.

The invention, furthermore, concerns a refractometric measurement device for operating the above-mentioned process, and that comprises a light source associated to a focussing lens used in order to create on the retina of the eye to be examined an image of the said source, a plurality of test lenses mounted on a rotary disc along a circle, the center of which coincides with that of the said disc, said test lenses being placed successively on the optical path between the eye and the focussing lens, a luminous intensity detector adapted to receive the rays emitted by the said image when they have passed through the interposed test lens and to transmit, for each interposed test lens, a luminosity signal to an electronic control element such as a microprocessor associated to registration and/or display means, identification means of the interposed test lens for which the said luminosity signal presents at least substantially a value sought, the said identification means also being connected to the said electronic element that controls a first motor driving the said rotary disc.

In related U.S. patent application Ser. No. 769,758, filed on Aug. 26, 1985 by the applicants of the present invention, said related application being a continuation of U.S. patent application Ser. No. 442,588, filed on Nov. 8, 1982, there is described an apparatus for refractometrically measuring the degree of spherical ametropia of a human eye placed at a location predetermined with respect to said apparatus, comprising:

(a) a light source;
(b) optical means for shaping light emitted by said source into a focussed light beam propagated along a light path and directing said beam to said eye in a given direction defined by an optical test axis coinciding with the optical axis of said eye, so as to produce on the retina of said eye an image of said light source;
(c) means interposed in said light path between said light source and the eye for intercepting light, in said light beam, in a concentric zone about said optical test axis, whereby the image of said light source formed on the retina is modified to contain an image of said zone of intercepted light;
(d) corrective testing lens presenting means adapted to interpose adjacent said eye successively any one of a plurality of corrective testing lenses of a single lens set across said light beam, said testing lenses having different respective optical power values;
(e) light detector means disposed and optically centered on said optical test axis and adapted to receive light reflected through the interposed testing lens by at least that area of the retina which contains said image of said zone of intercepted light; and
(f) signal generating and processing means associated with said lens presenting means and said light detector means and adapted to identify that one of said corrective testing lenses which, when interposed across said light beam by said lens presenting means, transmits to said light detector means the minimum amount of light reflected by said retina in response to said image of said zone of intercepted light. In practice, the earlier device gives entire satisfaction by supplying immediately and automatically, under the best possible conditions of comfort for the patient, perfectly precise indications concerning anomalies of sight, especially with respect to myopia (short-sightedness), presbyopia (loss of accomodation) and hypermetropia (long-sightedness), i.e. in the field of spherical ametropia cases. This device also allows, to a certain extent, to determine where necessary, the degree of non spherical ametropia especially the degree of astigmatism. It has been established, however, that the results obtained with the said device in this particular field (astigmatism and analog) leave possibilities for improvement, as concerns the precision required for calculating high quality corrective lenses.

The present invention therefore has the aim of creating a process and a device for refractometric measurement of the type indicated herein-above, that allows not only to measure instantaneously and automatically in a perfectly precise manner the degree of spherical ametropia of an eye, but also to determine at the same time, in an equally instantaneous and automatic way and with the same precision, the degree of non spheric ametropia especially the degree of astigmatism.

The process according to the present invention, that allows to achieve the desired aim, is noteworthy in that it consists, further to the operation phases indicated above, in interposing, between the focussing lens and the test lenses, on the path of the rays focussed towards the retina and the rays emitted by the said image, a "black optical slit" the periphery of which is defined at least in part by points located at inequal distances from a center of rotation situated on an axis of rotation substantially perpendicular to the plane of the said slit, this slit being provided in a screen and delimited at least in part by at least one reflecting surface, in order to cause to vary the angular position of the said slit and reflecting surface in the plane of the screen, by successive angular pitches about the said center of rotation which is, preferably, located substantially on the optical axis of the interposed test lens, and to raise the luminosity signal emitted by the detector for each rotation pitch of the said slit and reflecting surface about the said center.

One method of operating the process is noteworthy in that the source is placed on the optical axis of the eye, that is provided in the same screen, which is inclined at an angle predetermined with respect to this axis, a black optical slit defined by a reflecting opaque zone, and the said detector is positioned in such a way that it receives the rays emitted by the said image and reflected by the said reflecting zone, this image comprising a black zone that corresponds to the said black optical slit.

According to another advantageous operating embodiment, the said detector is placed substantially on the optical axis of the eye, a black optical slit defined between two reflecting zones, is provided in the said screen, that is inclined at an angle predetermined with respect to this axis, the said source is positioned in such a way that its rays, after having passed through the focussing lens, are reflected by the said reflecting zones towards the eye to be examined, the said detector receiving the rays emitted by the said image of the source, formed on the retina, image that comprises a black zone corresponding to the said black optical slit.

In one preferred variant according to the invention, the black optical slit is disposed, defined by the reflecting zone or between the reflecting zones in such a way that these slits and zones are inscribed within a circle, and the said screen is caused to turn by successive angular steps about an axis of rotation that is perpendicular to the plane of the screen and which passes through the center of the said circle.

The device according to the invention, for operating the process defined herein-above, is noteworthy, especially in that it comprises, interposed on the optical path between the test lens, on the one hand, and the focussing lens and the detector, on the other hand, a rotary opaque screen inclined at an angle preferably of 45° with respect to the optical axis of the interposed test lens and provided, in the intersection zone between this optical axis and the plane of the screen, with a black optical slit excentric with respect to the center of rotation of the screen and delimited at least partially by a minimum of one reflecting surface, the said screen being driven in rotation by a second motor, also controlled, where necessary, by the said electronic control element.

In one embodiment of the device according to the invention, the said motor is a motor operating step-by-step.

Advantageously, the respective optical axes of the source, of the focussing lens, of the interposed test lens and of the eye coincide so as to form a common optical axis, while the optical axis of the detector intersects preferably at an angle of 90°, the said common optical axis in a point that coincides with the said center of rotation of the screen, this latter being provided, in the zone surrounding the center with a black optical slit excentric with respect to this center and defined by a reflecting opaque surface.

In a preferred embodiment of the device according to the invention, the respective optical axis of the detector, of the interposed test lens and the eye coincide so as to form a common optical axis, while the optical axis of the whole formed by the source and the associated focussing lens intersects, preferably at an angle of 90°, the above-mentioned common optical axis in a point that coincides with the said center of rotation of the screen, this latter being provided, in the zone surrounding the said center, with a black optical slit delimited between two reflecting surfaces.

Due to the interposition, on the path of the focussed rays of the light source and the rays emitted by the image created on the retina of the eye to be examined, of at least one black optical slit with outlines not continuously in rotation, as defined herein-above, and due to the step-by-step rotation of this slit and to the increase for each rotation pitch, of the luminous intensity by using the above-mentioned detector, the device for operating the process according to the invention allows to determine the degree of non spherical ametropia—especially, the degree of astigmatism—with high precision, while supplying, with the same accuracy, the required indications concerning the various types of spherical ametropia, such as myopia, presbyopia and hypermetropia.

BRIEF DESCRIPTION OF THE DRAWINGS

The invention will be described in further detail herein-under, especially with reference to several examples of execution represented on the annexed figures, given only by way of non-limitative example, in which:

FIG. 1 represents schematically a first embodiment of the refractometry device according to the invention;

FIG. 2 represents, in a plane perpendicular to that of FIG. 1, the black optical slit defined by a reflecting surface, such as disposed in the device of FIG. 1;

DESCRIPTION OF THE PREFERRED EMBODIMENTS

Figures 3, 4:
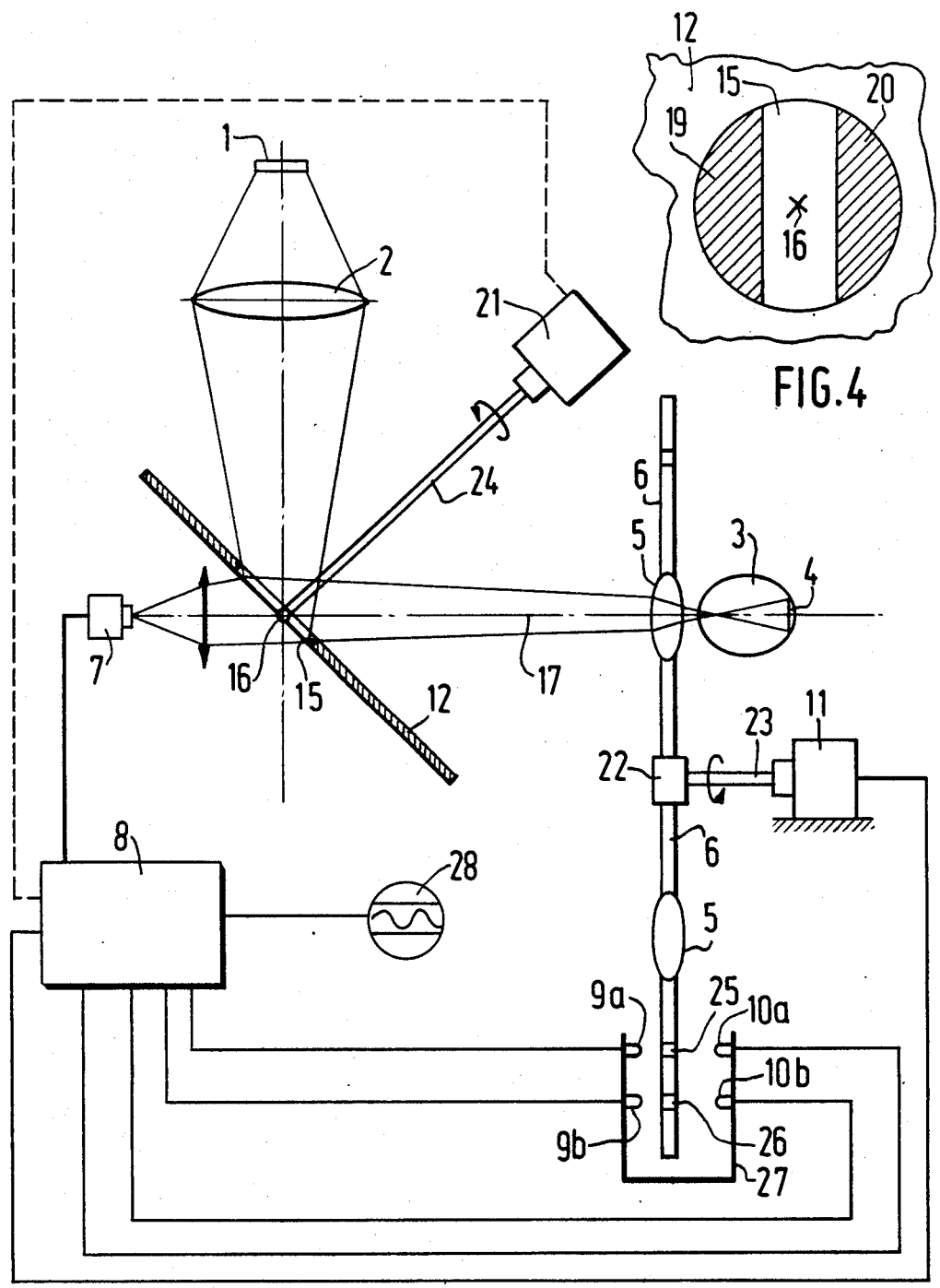
FIG. 3 is a scheme a another embodiment of the device according to the invention.
FIG. 4 represents in a plane perpendicular to that of FIG. 3, the black optical slit defined between two reflecting surfaces according to the disposition of the device of FIG. 3.

In the present specification, the term "black optical slit" designates a zone not transmitting towards the eye the rays of light, issuing from the source. It can be defined by an opaque zone when the source is positioned on the optical axis of the eye, or by a transparent zone when the optical axis of the source is shifted angularly with respect to that of the eye.

FIG. 1 shows a light source 1 associated to a focussing lens 2 that projects the rays of the source 1 towards the retina of an eye 3 to be examined to create thereupon a luminous image 4 of said source image that comprises especially a black zone corresponding to the "black optical slit" such as described herein-below. A rotary disc 6 bears a plurality of test lenses 5 having different optical characteristics, disposed with their optical centers equidistant on a circle the center 22 of which constitutes the center of rotation of disc 6. This latter is cinetically linked by any appropriate means, such as a shaft 23, to a step-by-step type motor 11 that drives the disc 6 so as to interpose successively, during a predetermined time period, the test lenses 5 between the eye 3 and the assembly of the source 1 and the focussing lens 2, the optical axis 17 of the interposed test axis coinciding, each time, with the common optical axis of source 1 and the focussing lens 2 axis that coincides, in turn, with the optical axis of the eye 3. The step-by-step motor 11 is electrically connected to an electric control element 8 such as a micro-processor or any other processing system that controls its operation according to a predetermined program.

The disc 6 is provided with a single synchronization hole 25 placed on a circle of center 22 wider than that which contains the respective optical centers of the test lenses 5. On another circle, concentric to the preceding one, the disc 6 comprises a number of reference holes 26 equal to the number of test lenses 5, each hole 26 corresponding to a determined lens 5. The disposition is such that when one of the test lenses 5 is correctly interposed between the eye 3 and the focussing lens 2, the reference hole 26 corresponding to this lens 5 is placed between a photodiode 9b and a phototransistor 10b mounted, as indicated on the figure, opposite facing on a fixed attachment or support 27, on either side of the disc 6. This attachment also bears another photodiode 9a and another phototransistor 10a disposed facing each other, between which the synchronization hole 25 is adapted to pass at each revolution of the disc 6. The photodiodes 9a, 9b and the phototransistors 10a, 10b are connected to an electronic element 8 which, due to the disposition described, identifies each test lens 5 when it is interposed between the eye 3 and the assembly of source 1 and of focussing lens 2.

An opaque screen 12 inclined at an angle of 45° with respect to the optical axis 17 is interposed between the eye 3 and any test lens 5 placed in front of the eye, on the one hand, and the assembly of the source and the focussing lens 2, on the other hand. This screen is displacable in step-by-step rotation about a center 16 situated on the optical axis 17 that, as will appear from what is described hereinabove, is common to the source 1, the focussing lens 2, the eye 3 and the interposed test lens 5 (i.e. placed in front of the eye). The driving in step-by-step rotation of the screen 12 is ensured by a motor 21 connected to the screen by any appropriate cinematic means, such as a shaft 24.

As shown by FIG. 2 the screen 12 comprises, inscribed in a circle about center 16 two transparent zones 13, 14 located on either side of the center 16 and separated by an opaque, reflecting surface 18 the center of which coincides with the center 16. It will be observed that the outline of the reflecting surface 18 is formed of points situated at respective variable distances from the center 16 and which, consequently, for each rotation of the screen 12, the angular position on the retina, of the black zone of the image 4, that corresponds to the reflecting surface 18, is different.

The reflecting surface 18 sends back the luminous rays emitted by the image 4 created on the retina towards a detector of luminous intensity 7 electrically connected to the electronic element 8 and producing a signal that represents the luminous intensity of the above-mentioned rays. When, for a given angular position of the screen 12 with respect to its center 16, the interposition of a test lens 5 provokes a minimum luminosity of the detector 7, this indicates—given the optical laws relating to the rays reflected in the same direction as the optical axis of their incidence on a reflecting surface—that the involved test lens causes to coincide, at least substantially, the punctum remotum of the eye examined with the optical plane of the detector. Due to this, the practitioner can determine in a manner known per se the optical characteristics required of a corrective lens used to overcome the spherical ametropia of the eye, such as described in the above-mentioned French patent application.

The present invention concerns a device that allows, furthermore, to determine with precision the degree of non spherical ametropia, especially the degree of astigmatism. With this purpose, the screen 12 is caused to turn step-by-step (thus the assembly of the transparent zones 13, 14 and the reflecting opaque surface 18) about the center 16, which provokes in the presence of an astigmatism, variations of intensity of luminosity of the rays received by the detector 7, variations that are superimposed on those due to the succession of the test lenses 5. The corresponding luminosity signals are transmitted by the detector 7 to the electronic control element 8 that is connected to a registration and/or display device 28 supplying the practitioner, in any appropriate form, with the values that he needs to determine the characteristics of the required corrective lens.

The embodiment represented on FIGS. 3 and 4, where the same numerical references as those of the preceding figures are used to designate identical or analog elements, is based on the same principle as the execution example described herein-above.

In this embodiment, however, the assembly of the source 1 and the focussing lens 2 is not placed on the optical axis 17, behind the screen 12 (with respect to the eye 3), but the luminosity detector 7 is so placed. Furthermore, the assembly of the source 1 and the focussing lens 2 is disposed, in the present embodiment, in the place which was occupied by the detector 7 in the preceding example (FIG. 1).

In this embodiment, the screen 12 comprises, inscribed in a circle of center 16, two reflecting opaque surfaces 19, 20 having a form and disposition analog to those of the two transparent zones 13, 14 indicated on FIG. 1, as well as a transparent zone 15 having a form and disposition analog to that of the reflecting surface 18 according to FIG. 1. It will be noted, in this variant, that the outline of the transparent zone 15 is formed by points separated by inequal distance from the center 16 of rotation of the screen 12, and that the results obtained with this embodiment are the same as those described hereinabove with reference to FIGS. 1 and 2, although in the present case (FIGS. 3 and 4), contrary to the example according to FIGS. 1 and 2, the rays of the source 1, focussed by the focussing lens 2, are reflected by reflecting surfaces 19, 20 towards eye 3 (through the interposed test lens 5), while the rays emitted by the image created on the retina of the eye 3 pass through the transparent zone 15, along the optical axis 17, to arrive at the detector 7.

Of course, the present invention is in no way limited to the embodiments described and represented; it can be adapted to numerous variants available to the man skilled in the art without departing from the spirit and scope of said invention.

In the two embodiments described, a luminous image 4 is thus obtained on the retina, said image comprising a black zone that corresponds to a "black optical slit" defined, either by an opaque and reflecting zone (FIGS. 1 and 2), or by a transparent zone (FIGS. 3 and 4).

The device according to the invention can especially be utilized as a focometer.

With this aim, it is sufficient to associate to the device that is described herein-above and represented on the figures, a focussing lens and a screen as well as a support adapted to receive the corrective lenses the power of which it is required to measure, these three elements being disposed along the optical axis 17 of the device according to the rotary disc 6, on the trajectory of the incident beam.

We claim:

1. An apparatus for refractometrically measuring the degree of ametropia and astigmastism of an eye, placed at a location predetermined with respect to said apparatus, comprising:
   (a) a light source;
   (b) optical means for shaping light emitted by said source into a focussed light beam propagated along a light path and directing said beam to said eye in a given direction defined by an optical test axis coinciding with the optical axis of said eye, so as to produce on the retina of said eye an image of said light source;
   (c) corrective testing lens presenting means adapted to interpose adjacent said eye, successively any one of a plurality of corrective testing lenses of a lens set across said light beam, said testing lenses having different respective optical power values;
   (d) circular screen means interposed in said light path between said light source and the eye for intercepting said light beam, said screen means being rotatably mounted on an axis thereof which passes through said optical test axis, said screen means and said axis thereof being inclined at an angle with respect to said optical test axis, said screen means including a black slit system with at least one opaque reflecting zone and at least one open zone, said zones being shaped in order to obtain an image of said source on said retina, the thus modified image of the source being reflected by said retina through said corrective test lens and said screen means to obtain a second image in a given plane;
   (e) means for rotating said screen means about the axis thereof in successive angular pitches;
   (f) light detector means disposed in said plane and centered on the axis of the beam reflected by the retina through said corrective test lens and said screen means, said detector means emitting a luminous intensity signal; and
   (g) signal generating and processing means, associated with said lens presenting means, said means for causing said screen to turn, and said light detector means, for identifying that one of said corrective testing lenses which, when interposed across said test light beam by said lens presenting means, and depending upon the orientation of said black slit system, results in said light detector means producing a luminous intensity signal substantially equal to a desired value.

2. An apparatus according to claim 1; in which the light source, the optical means, the center of the circular screen means and the eye are placed on the optical test axis, the screen means presenting a central opaque reflecting zone between two open zones, the light beam reflected by the retina through the test lens centered on said axis and reflected by the central zone of the screen means and reaching the light detector means along a luminous path presenting a given angle with said optical test axis.

3. An apparatus according to claim 1; in which the light source, the optical means and the center of the circular screen means are on a first optical axis, the screen means presenting a central open zone between two opaque reflecting zones, the light beam issuing from the light source and the optical means being reflected by said reflecting zone toward the eye along the optical test axis, the light beam reflected by the retina through the test lens centered on said optical test axis passing through said open zone to reach the light detector means and centered on said optical test axis.

4. Apparatus according to claim 1; for use as a focometer in which, on the optical test axis after the rotating circular screen means, are placed a focussing lens, a screen, and a support for the corrective test lens, the focal distance of which must be measured.

5. A process of measurement of the degree of ametropia and astigmatism of an eye, comprising the steps of:
   causing luminous rays, issuing from a light source, to pass through focussing means toward the retina of the eye to be examined, in order to create an image of said source;
   modifying said image by providing on the path of the light between the light source and the eye a rotating disc presenting a circle centered on the axis of said source and said focussing means, and on the optical axis of the eye maintained in a firm position and considered as the optical axis, said rotating disc presenting a black slit having at least one opaque reflecting zone and at least one open zone in order to modify said image, said rotating disc being inclined at an angle with respect to said optical axis;
   rotating said rotating disc about the center of said circle in successive angular pitches;
   interposing one of a set of corrective testing lens on said optical test axis close to the eye;
   sending the modified image reflected by the retina, to a luminous intensity detector through the corrective testing lens and the rotating disc;
   producing a luminous signal in response to detection by said detector;
   transmitting the luminous signal issuing from the detector to signal generating and processing means; and
   processing the luminous intensity and controlling the selected corrective testing lens and the angular position of the rotating disc, the result being considered as good when the luminous signal is minimum, the plane of the luminous intensity detector being then substantially at the punctum remotum of the eye.

* * * * *